United States Patent [19]

White et al.

[11] Patent Number: 4,803,207

[45] Date of Patent: Feb. 7, 1989

[54] HYPOGLYCEMIC 2',3',10'-TETRAHYDRO-10'-HYDROXY-10'-SUBSTITUTED-SPIRO[CYCLOAKANE-1,3'-PYRIMIDO(1,2-A)INDOLE]DERATIVES

[75] Inventors: Alan C. White, Englefield Green; Ian A. Cliffe, Cippenham; Richard S. Todd, Burnham, all of England

[73] Assignee: John Wyeth & Brother Ltd., Maidenhead, England

[21] Appl. No.: 23,333

[22] Filed: Mar. 9, 1987

[30] Foreign Application Priority Data

Mar. 13, 1986 [GB] United Kingdom ............... 8606254

[51] Int. Cl.$^4$ ................ C07D 487/04; A61K 31/505
[52] U.S. Cl. ..................................... 514/267; 544/231; 546/201; 548/410; 548/485
[58] Field of Search ................... 514/267; 544/231

[56] References Cited

U.S. PATENT DOCUMENTS

| 2,984,666 | 5/1961 | Bortnick et al. | 544/252 |
| 3,634,426 | 1/1972 | Eberle | 544/230 |
| 3,891,644 | 6/1975 | White | 544/230 |

FOREIGN PATENT DOCUMENTS 1366133  9/1974  United Kingdom ............... 544/252

Primary Examiner—Donald G. Daus
Assistant Examiner—E. Bernhardt
Attorney, Agent, or Firm—Richard K. Jackson

[57] ABSTRACT

Pyrimidoindoles of formula (I)

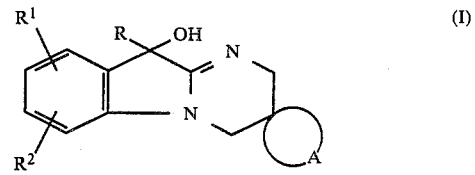

and their pharmaceutically acceptable acid addition salts, wherein R represents lower alkyl a mono- or bicyclic aryl radical or a group of mormula $R^3O$—B—[- where $R^3O$ is (lower)alkoxy,aryl(lower)alkoxy or hydroxy and B is a lower alkylene chain optionally containing one double or triple bond], $R^1$ and $R^2$ which may be the same or different each represent hydrogen, hydroxyl, lower alkyl, lower alkoxy, halo(lower)alkyl, halogen, amino or mono- or di(lower) alkylamino and A, together with the carbon atom to which it is attached, represents 5, 6 or 7 membered saturated carbocyclic or heterocyclic ring, are useful as hypoglyceamics.

10 Claims, No Drawings

HYPOGLYCEMIC 2',3',10'-TETRAHYDRO-10'-HYDROXY-10'-SUBSTITUTED-SPIRO[CYCLOAKANE-1,3'-PYRIMIDO(1,2-A)INDOLE]DERATIVES

This invention relates to substituted pyrimidoindoles, to processes for their preparation, to their use and to pharmaceutical compositions containing them.

The novel compounds of the present invention are pyrimidoindoles of the general formula (I)

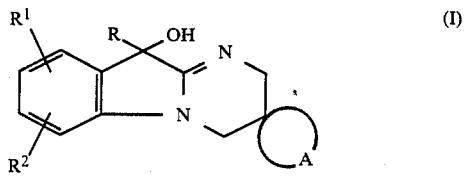

and their pharmaceutically acceptable acid addition salts. In the formula, R represents lower alkyl, a mono- or bicyclic aryl radical or a group of formula $R^3O$-B- [where $R^3O$ is (lower)alkoxy, aryl(lower)alkoxy or hydroxy and B is a lower alkylene chain optionally containing one double or triple bond], $R^1$ and $R^2$ which may be the same or different each represent hydrogen, hydroxyl, lower alkyl, lower alkoxy, halo(lower)alkyl, halogen, amino or mono- or di(lower)alkylamino and A, together with the carbon atom to which it is attached, represents 5, 6 or 7 membered saturated carbocyclic or heterocyclic ring.

The term "lower" as used herein means that the radical referred to contains 1 to 6 carbon atoms. Preferably such radicals contain 1 to 4 carbon atoms. For example, a lower alkyl group may be methyl, ethyl, propyl or butyl and a lower alkoxy may be methoxy, ethoxy, propoxy or butoxy.

The term "aryl" is used herein to denote a radical having an aromatic character. Such radicals include phenyl, naphthyl and heterocyclic radicals having an aromatic character. For example, when R is an aryl radical it may be a radical such as phenyl, naphthyl, furyl, thienyl, pyridyl, indolyl and benzothienyl, each of which may be substituted or unsubstituted. Suitable substituents include those mentioned herein for the definitions of $R^1$ and $R^2$; preferable substituents are halogen (for example fluorine, chlorine or bromine), lower alkyl (for example methyl, ethyl, propyl or butyl), lower alkoxy (for example methoxy, ethoxy, propoxy or butoxy) and halo(lower)alkyl (for example trifluoromethyl). Preferably R is phenyl optionally substituted as mentioned above or lower alkyl (e.g. butyl).

Preferred examples of $R^1$ and $R^2$ residues include hydrogen, lower alkyl (e.g. methyl, ethyl, propyl and butyl), lower alkoxy (e.g. methoxy, ethoxy, propoxy and butoxy), halo(lower)alkyl (e.g. trifluoromethyl) and halogen (e.g. chlorine and bromine).

When $R^3O$ is an aryl(lower)alkoxy group, the aryl radical is preferably a phenyl group which may optionally be substituted by, for example, the substituents defined above in respect of $R^1$ and $R^2$. For example $R^3O$ may be an optionally substituted benzyloxy group. Examples of suitable $R^3O$-B- groups include 3- or 4-methoxybutyl, 4-ethoxybutyl, 3-methoxy-2-methylpropyl and 3-hydroxyl-propynyl.

When A, together with the carbon atom to which it is attached, represents a carbocyclic ring, the radical A is an alkylene chain; one or more carbon atoms in the chain may be substituted by, for example, one or two lower alkyl groups. Preferably A represents $-(CH_2)_n-$ where n is 4, 5 or 6. When A, together with the carbon atom to which it is attached, represents a saturated heterocyclic ring, the heterocylic ring may contain one or more hetero atoms such as oxygen or nitrogen. Examples of heterocyclic rings include piperidine, pyrolidine, tetrahydropyran and tetrahydrofuran. A nitrogen heteroatom may, if desired, be substituted by, for example, a lower alkyl group or a protecting group (such as 1,1-dimethylethoxycarbonyl, benzyl or trimethylsilyl) which can be removed to give a compound in which the nitrogen atom is unsubstituted.

Examples of preferred compounds of the invention are:

2', 3', 4', 10'-tetrahydro-10'-hydroxy-10'-phenylspiro[cyclohexane-1,3'-pyrimido(1,2-a)indole]

2', 3', 4', 10'-tetrahydro-10'-hydroxy-10'-phenylspiro[cycloheptane-1,3'-pyrimido(1,2-a)indole]

2', 3', 4', 10'-tetrahydro-10'-butyl-10'-hydroxyspiro[cyclohexane-1,3'-pyrimido(1,2-a)indole]

2',3', 4', 10'-tetrahydro-10'-hydroxy-10'-phenylspiro[cyclopentane-1,3'-pyrimido(1,2-a)indole]

2',3',4', 10'-tetrahydro-10'-hydroxy-10'-phenylspiro[piperidine-4,3'-pyrimido(1,2-a)indole]

and the pharmaceutically acceptable salts thereof.

The compounds of the invention may be prepared by a process in which a ketone of general formula (II)

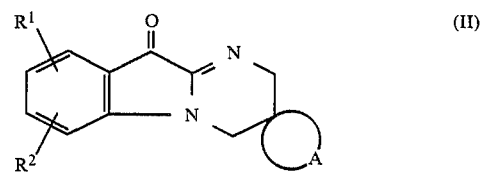

where $R^1$, $R^2$ and A have the meanings given above is reacted with an organometallic compound containing a $R^4$ residue where $R^4$ represents lower alkyl, a mono- or bicyclic aryl radical or a group of formula $R^{3'}$—O—B—[where $R^{3'}$ is (lower)alkoxy, aryl(lower)alkoxy or protected hydroxy such as tetrahydropyranyloxy, trialkylsiloxy or benzyloxy and B is as defined above-]and where $R^{3'}$—O—is a protected hydroxy group removing the protecting group to give a product in which $R^{3'}O$ is hydroxy. The organometallic compound can be, for example, a Grignard reagent of formula $R^4MgY$ where $R^4$ has the meaning given above and Y is halogen or an alkalimetal compound such as a lithium derivative of formula $R^4Li$ (e.g. phenyl lithium). The reaction with the organometallic compound is generally carried out in an inert organic solvent.

The ketones of general formula (II) may be prepared by known processes, for example those disclosed in UK Specification No. 1,366,133. For example, a substituted isatin of general formula (III)

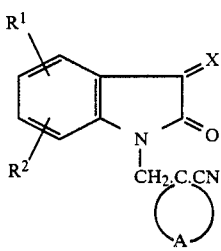

(III)

where $R^1$, $R^2$ and A are as defined above and X is a protected oxo group, such as a ketalized oxo group (e.g. ethyleneketal, propyleneketal or dimethoxy) may be hydrogenated e.g. in presence of a hydrogenation catalyst to give an amine of general formula (IV)

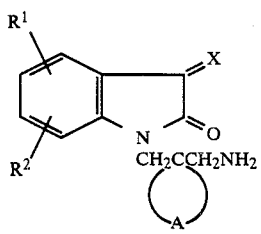

(IV)

where $R^1$, $R^2$, A and X have the meanings given above. The amine may be cyclodehydrated to a compound of general formula (V)

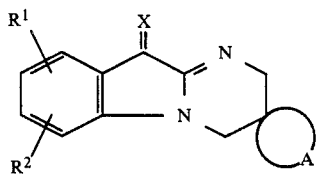

(V)

where $R^1$, $R^2$, A and X have the meanings given above. The amine may be cyclodehydrated by, for example, heating in an inert organic solvent. In general, the substituted isatin of general formula (III) may be hydrogenated to the compound of formula (V) without isolation of the intermediate amine of general formula (IV).

The compound of formula (V) can be converted to the ketone of formula (II) by deprotecting the protected keto group, e.g. by hydrolysis of a ketalised oxo group.

The starting substituted isatin of formula (III) may be prepared by, for example, condensing a 3-halopropanenitrile of general formula (VI)

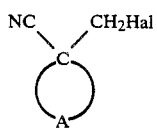

(VI)

where A has the meaning given above and Hal is chloro or bromo with a compound of general formula (VII)

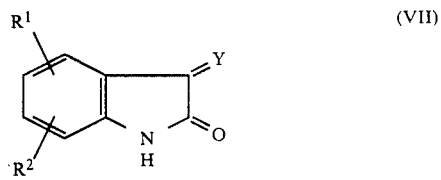

(VII)

where $R^1$ and $R^2$ have the meanings given above and Y is oxo or protected oxo and, where Y is oxo, protecting the oxo group in the resulting product. The condensation may be carried out in presence of a base, e.g. potassium tertiary butoxide or sodium or potassium hydride in a solvent such as dimethylsulphoxide, dimethylfuranamide or N-methyl-2-pyrrolidone. The 3-halopropanenitriles can be prepared by known methods or by condensing a corresponding 2-substituted-ethanenitrile with bromochloromethane, dibromomethane or dichloromethane in presence of a non-nucleophilic strong base such as lithium diisopropylamide.

An alternative method of preparing the compounds of the invention comprises cyclodehydrating an indole derivative of the general formula (VIII)

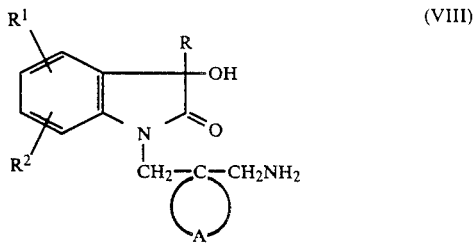

(VIII)

wherein R, $R^1$, $R^2$ and A have the meanings given above.

The compound of general formula (VIII) in its free base form or as an acid addition salt thereof may be cyclodehydrated to the compound of general formula (I) by heating it, for example, in an inert organic solvent. The solvent can be, e.g. xylene or odichlorobenzene, and the heating can be carried out at the reflux temperature. It is preferred to carry out the cyclisation in the presence of a catalytic amount of an acid catalyst, e.g. p-toluene sulphonic acid or benzene sulphonic acid.

The indole compounds of general formula (VIII) and their acid addition salts can be prepared by the hydrogenation of a nitrile compound of general formula (IX)

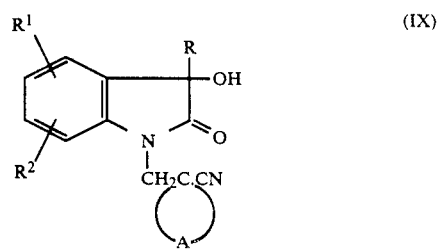

(IX)

wherein R, $R^1$, $R^2$ and A have the meanings given above.

The hydrogenation may be carried out in the presence of a hydrogenation catalyst. Elevated temperatures and pressures may be employed. However, if the compound of formula (IX) contains any substituents $R^1$ and $R^2$, such as halogen atoms, which are liable to be effected by drastic hydrogenation conditions, the hydrogenation should be carried out under mild conditions. For example, a nickel catalyst [such as Raney nickel, e.g. Raney nickel W2 (Org.Syn.Coll.Vol. III,1955, 181)]can be employed, e.g. in presence of ammonia and ethanol, and the hydrogenation carried out at relatively low pressures (e.g. about 40 p.s.i.)and temperatures (e.g. about 40° to 50° C.).

In general, the intermediate of formula (VIII) is not isolated from the reaction medium and hydrogenation of the nitrile of formula (IX) gives the compounds of the invention directly.

The nitrile compounds of general formula (IX) can be prepared by condensing an oxindole of general formula (X)

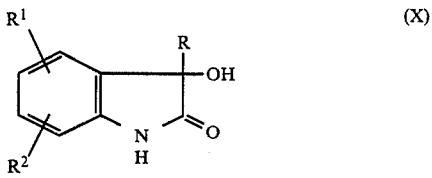

wherein R, $R^1$ and $R^2$ have the meanings given above with a chloropropanenitrile of general formula (VI) given above in the presence of a base.

A further process for preparing the compounds of the invention comprises cyclising a compound of general formula (XI)

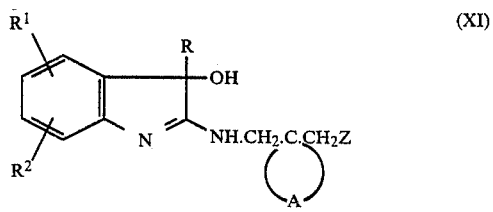

or an acid addition salt thereof, wherein R, $R^1$, $R^2$ and A are as defined above and Z is a halogen atom, preferably chlorine. The process may be carried out as described in UK Specification No. 1,450,543.

In yet another process for preparing the compounds of the invention an indole of general formula (XII)

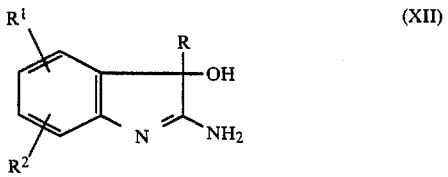

where R, $R^1$ and $R^2$ have the meanings given above, is condensed with a dihaloalkane of general formula

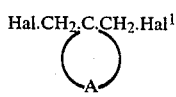

Hal.CH$_2$.C.CH$_2$.Hal$^1$ where A has the meaning given above and Hal and Hal$^1$ are each chlorine, bromine or iodine. The process may be carried out as described in UK Specification No. 1,427,066.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess at least one asymmetric carbon atom and hence can exist in various stereochemical forms. The stereochemical forms can be separated or isolated by standard procedures. For example resolution of a racemic final product or intermediate may be carried out by known procedures so as to give the product as an optically active enantiomorph.

The compounds of the present invention possess pharmacological activity. For example, the compounds in general possess hypoglycaemic activity and hence are of value in the treatment of diabetes. The compounds of the invention are tested for hypoglycaemic activity by a standard procedure in which the compounds are administered to rats and the blood glucose concentration is determined prior to administration and at various times after dosage. When 2', 3', 4', 10'-tetrahydro-10'-hydroxy-10'phenylspiro[cyclohexane-1,3'-pyrimido[1,2-a]indole], a representative compound of the invention, was tested by this procedure at 100 mg/kg p.o. the blood glucose concentration was found to be 76% and 65% of the control animals (i.e. rats administered vehicle alone) at 2 hours and 4 hours respectively after administration.

The invention further provides a compound of formula (I) or a pharmaceutically acceptable acid addition salt for use as a hypoglycaemic in a mammal.

The invention also provides a pharmaceutical composition comprising a compound of general formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aids binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

3',4'-Dihydrospiro[cyclohexane-1,3'-pyrimido(1,2-a)indol-10'(2'H)-one]

(a)
1-[1'-[2'(3'H)-oxospiro(1,3-dioxolane)-2,3'-indolyl]-]methyl cyclohexane carbonitrile Spiro[1,3-dioxolane)-2,3'-indol-2'(3'$\underline{H}$)-one](1.91g)was added portionwise to a stirred solution of potassium t-butoxide (1.34g) in dry DMSO (20 ml) under nitrogen. After 10 min, 1-chloromethylcyclohexanecarbonitrile (1.96g) was added dropwise and the solution heated at 130° for 24 h. The solution was cooled, poured into ice-water (100 ml), and stirred vigorously for 18 h. The solid was separated, dried, and recrystallised from propan-2-ol to give the title compound (1.4 g), m.p. 130°-130.5°.

Found : C, 69.0; H, 6.7; N, 8.8%; $C_{18}H_2ON_2O_3$ requires: C, 69.2; H, 6.45; N, 9.0%.

(b) 2', 3', 4', 10'-Tetrahydro(1,3-dioxolane)-2-spiro-10'-pyrimido[1,2-a]indole-3'-spirocyclohexane Ethanolic ammonia (100 ml) and one spatula Raney nickel were added to a solution of 1-[1'-[2'(3'H)-oxospiro (1,3-dioxolane)-2,3'-indolyl]]methylcyclohexane carbonitrile(1.25 g) in ethanol (100 ml). The mixture was hydrogenated at 50° C. at 4-5 atm. (about $3.9\times10^5$–$4.9\times10^5$ Pa) for 2 hours. After cooling to room temperature it was filtered through Kieselguhr, and the solution was concentrated in vacuo to give the crude product (1.23 g). The product was re-dissolved in ether(60ml), filtered through Kieselguhr,and concentrated in vacuo. The product was recrystallised from hexane to give a first crop of the title compound as the free base (0.36 g) m.p. 71°-107° C.

Found: C, 72.30; H, 7.55; N, 9.56%; $C_{18}H_{22}N_2O_2$ requires C, 72.45; H, 7.45; N, 9.40%.

Further material was obtained by chromatography of the mother liquors on $SiO_2$ eluting with EtOAc.

(c) 3',4'-Dihydrospiro[cyclohexane-1,3'-pyrimido [1,2-a]indol-10'(2'H)-one]

A solution of the compound of Example 1(b) (4.4 g) in hexane (3 ml) was added dropwise to concentrated $H_2SO_4$ (25 ml) at 30°. The solution was kept at room temperature and after 1 hour poured onto ice. The solution was basified with concentrated aqueous ammonia and at pH7 a brown precipitate formed. The solution was decanted and further basified with concentrated aqueous ammonia to pH9. The precipitate was filtered, washed with aqueous ammonia and dried in vacuo. A solution of the solid in EtOAc was passed down a silica column and the solvent evaporated to give crystals of the title compound (1.4 g), m.p.138°-143°.

Found: C, 74.5; H, 7.3; N, 10.8%; $C_{16}H_{18}N_2O\frac{1}{4}H_2O$ requires: C, 75.6; H, 7.1; N, 11.0%.

EXAMPLE 2

2',3',4',10'-Tetrahydro-10'-hydroxy-10'-phenylspiro [cyclohexane-1,3'-pyrimido(1,2-a)indole]

Bromobenzene (10 drops; from 2.6 g) was added dropwise to stirred magnesium turnings (0.38 g) in diethyl ether (10 ml) under nitrogen. When the reaction commenced a solution of the remaining bromobenzene in diethyl ether (3 ml) was added dropwise to maintain reflux. The mixture was heated under reflux until little magnesium remained, then cooled and a solution of 3', 4'-dihydrospiro-[cyclohexane-1,3'-pyrimido(1,2-a)indol-10(2H)-one](1.4 g) in dichloroethane (20 ml) added dropwise. After 1 hour the reaction mixture was poured onto water (100 ml), extracted with chloroform (2 × 100 ml), the chloroform extracts combined, dried ($MgSO_4$) and evaporated under reduced pressure to give a solid. Trituration of the solid with diethyl ether, followed by recrystallisation from ethyl acetate gave the title compound (0.85 g). Ethereal hydrogen chloride was added to a solution of the title compound in propan-2-ol, giving the title compound in the form of the hydrochloride

EXAMPLE 3

2',3',4',10'-Tetrahydro-10'-hydroxy-10'-phenylspiro[cycloheptane-1,3'-pyrimido(1,2-a)indole]

(a)

1-[1-(3-Hydroxy-2(3H)-oxo-3-phenylindolyl)methyl]-cycloheptanecarbonitrile

3-Hydroxy-3-phenylindol-2(1H)one (9.0 g), was added portionwise to a stirred solution of potassium tertbutoxide (4.9 g) in dimethyl sulphoxide (100 ml) under an atmosphere of nitrogen. After 10 min, 1-chloromethylcycloheptanecarbonitrile (6.9 g) was added rapidly. The solution was heated to 130° for 18 h, cooled, and poured into water (500 ml). The aqueous mixture was extracted with diethyl ether (3×200 ml); the organic extracts dried (MgSO$_4$) and evaporated in vacuo to ca. half volume to give a white precipitate of the title compound (1.94 g). Further washing of the drying agent with chloroform and evaporation in vacuo gave more of the title compound (1.8 g). A small sample was recrystallised from propan-2-ol; m.p. 202.5°–203.5°.

Found: C,76.1; H, 6.8; N, 7.5%; $C_{23}H_{24}N_4O_2.\frac{1}{4}H_2O$ requires: C, 75.7; H, 6.8; N, 7.7%.

(b)

2',3',4',10'-Tetrahydro-10'-hydroxy-10'-phenyl-spiro[cycloheptane-1,3'-pyrimido(1,2-a)indole]

A mixture of the compound of Example 3(a) (4.0 g) and Raney nickel (1 small spoonful) in 50% saturated ethanolic ammonia (200 ml) was heated at 50° under an hydrogen atmosphere (approx. 50 psi, about $3 \times 10^5$ Pa) for 7 hours. The mixture was cooled, filtered through Kieselguhr, and the filtrate evaporated under reduced pressure to give a gum (3.6 g). Trituration of the gum with EtOAc gave a solid (2.43 g). The filtrate was evaporated under reduced pressure to give an oil which was triturated with EtOAc to give a solid (0.43 g). The solid from the first trituration (2.43 g) was chromatographed (basic Al$_2$O$_3$;CHCl$_3$) and the gum triturated with EtOAc to give a solid (1.45 g). A solution of the combined solids (1.88 g) in MeOH was treated with etheral hydrogen chloride and evaporated under reduced pressure to give an oil which was triturated with Et$_2$O to give the title compound as the hydrochloride (1.93 g), m.p. 267° (dec).

Found: C, 72.2; H, 6.9; N, 7.5%; $C_{22}H_{26}N_2O.HCl$ requires: C, 71.8; H, 6.8; N,7.3%.

EXAMPLE 4

2', 3',4',10'-Tetrahydro-10'-butyl-10'-hydroxyspiro[cyclohexane-1,3'-pyrimido(1,2-a)indole]

(a) 3-Butyl-3-hydroxyindole-2(3H)-one (3.4 g) was added portionwise to a solution of potassium t-butoxide (1.9 g) in dry, deoxygenated dimethyl sulphoxide (30 ml). To this was added 1-chloromethylcyclohexanecarbonitrile (3.2 g). The mixture was heated to 130° for four days. and then poured onto ice. Extraction with ethyl acetate, washing with water, drying (MgSO$_4$) and evaporation in vacuo gave an impure oil which was purified by chromatography on silica eluting with ether. Crystallisation from ethyl acetate/hexane and recrystallisation from cyclohexane gave 1-[1-(3-butyl-3-hydroxy-2(3H)-oxo-indolyl)methyl]cyclohexanecarbonitrile as crystals (5.4 g) m.p. 124°–5°.

(b) The crystals from Example 4(a) were hydrogenated in saturated ethanolic ammonia (200 ml) with Raney nickel under a hydrogen atmosphere (40 p.s.i; about $2.7 \times 10^5$Pa). After removal of the catalyst, evaporation in vacuo and trituration with ethyl acetate gave the title compound as colourless crystals (2.0 g) m.p. 192°–5°.

Found: C, 67.9; H, 93; N, 7.2%; $C_{20}H_{28}N_2O.HCl.2/3C_3H_8O$ requires: C, 67.9; H,8.9; N,7.2%.

EXAMPLE 5

2', 3', 4', 10'-Tetrahydro-10'-hydroxy-10'-phenylspiro[cyclopentane-1,3'-pyrimido(1,2-a)indole]

(a) 3-Hydroxy-3-phenylindol-2(3H)-one (11.50 g) was added portionwise to a stirred solution of potassium tert-butoxide (6.30 g) in dry, deoxygenated dimethyl-sulphoxide (125 ml) under nitrogen. After 0.5 hour 1-chloromethylcyclopentanecarbonitrile (7.18 g) was added and the solution heated at 120° for 17 hours, cooled to room temperature, and poured into water (500 ml). The mixture was extracted with ethylacetate (3×250 ml). The extracts were washed with water (100 ml), dried (MgSO$_4$), and evaporated under reduced pressure to give a gum which was triturated with diethyl ether to give 1-[1-(3-Hydroxy-2 (3H) -oxo-3-phenylindolyl)methyl]cyclopentane carbonitrile as a crystalline solid (9.49 g), m.p. 155°–157°.

Found: C, 75.6; H, 6.25; N, 8.2%; $C_{21}H_{20}N_2O_2$ requires C, 75.9; H, 6.1; N, 8.4%.

(b) A mixture of 1-[1-(3-Hydroxy-2(3H)-oxo-3-phenylindolyl)methyl]cyclopentane carbonitrile (8.3 g) and Raney nickel (2 spatula spoons) in 50% saturated ethanolic ammonia (200 ml) was heated at 50° under a hydrogen atmosphere (50 p.s.i; about $3 \times 10^5$Pa) for 18 hours. The mixture was cooled, filtered through Kieselguhr, and evaporated under reduced pressure to give a solid which was purified by trituration with ethylacetate, chromatography (basic Al$_2$O$_3$; chloroform), and trituration with ethyl acetate to give the title compound (5.9 g).

A solution of the title compound in methanol was treated with ethereal hydrogen chloride and evaporated under reduced pressure to give a solid which was washed with diethyl ether and air dried to give the title compound as the hydrochloride (6.2 g), m.p. 263°–264° (dec).

Found: C, 70.7; H, 6.7; N, 7.9%; $C_{21}H_{22}N_2O.HCl$ requires: C, 71.1; H, 6.5; N, 7.9%.

EXAMPLE 6

2', 3', 4', 10'-Tetrahydro-10'-hydroxy-10'-phenyl-spiro(piperidine-4,3'-pyrimido[1,2-a]indole)

(a) 3-Hydroxy-3-phenylindol-2(3H)-one (5.05 g) was added portionwise to a stirred solution of potassium tert-butoxide (2.77 g) in dry deoxygenated dimethyl-sulphoxide (60 ml) at room temperature under nitrogen. After 0.5 hour tert-butyl-4-chloromethyl-4-cyano-piperidine-1-carboxylate (5.7 g) was added portionwise and the solution heated at 120° for 17 hours, cooled to room temperature, poured into water (250 ml), and extracted with ethylacetate (3×250 ml). The organic phase was dried (MgSO$_4$) and evaporated under reduced pressure to give an oil. Purification by chromatography [SiO₂; methanol-chloroform (2:98)]gave a solid which was triturated with hot cyclohexane to give 1,1-dimethylethyl-4-[1-(3-hydroxy-2(3H)-oxo-3-phenylindoyl) methyl]-4-cyanopiperidine-1-carboxylate (5.5 g), m.p. 197.5°-198° (dec) (from ethyl acetate).

Found: C, 70.0; H, 6.6; N,9.75%; $C_{26}H_{29}N_3O_4$ requires: C, 69.8; H, 6.5; N, 9.4%.

(b) A mixture of 1,1-dimethylethyl-4-[1-(3-hydroxy2(3H)-oxo-3-phenylindolyl)methyl]-4-cyanopiperidine-1carboxylate (4.8 g) and Raney nickel (1 spatula spoon) in 50% saturated ethanolic ammonia (200 ml) was heated to 50° under a hydrogen atmosphere (50 p.s.i; about $3 \times 10^5$ Pa) for 17 hours. The mixture was cooled, filtered through Kieselhuhr, and the solution evaporated under reduced pressure. The residue was purified by chromatography (basic Al₂O₃; chloroform)to give a solid which was triturated with ethyl acetate to give 2',3',4',10'-tetrahydro-10'-hydroxy-10'-phenyl-1-(1,1-dimethyl)ethoxycarbonylspiro(piperidine-4,3'-pyrimido[1,2-a]indole) (2.8 g), m.p. 209°-210° (dec).

Found: C, 72.2; H, 7.5; N,9.3%; $C_{26}H_{31}N_3O_3$ requires C, 72.0; H, 7.2; N, 9.7%.

(c) A suspension of the product of example 6(b) (2.8 g) in ethanolic hydrogen chloride (50 ml) was warmed to effect solution. After 10 min, the solvent was evaporated in vacuo and the residual gum dissolved in a small quantity of methanol. Toluene was added and the solvents evaporated in vacuo to leave a white solid (2.8 g). Recrystallisation from ethanol gave the title compound dihydrochloride (2.4 g) m.p.>300° (dec).

Found: C, 58.9; H, 6.7; N, 9.6. ; $C_{21}H_{23}N_3.2HCl.1.25H_2O$ requires: C, 58.8; H, 6.4;N,9.8%.

EXAMPLE 7

(−) and
(+)-2',3',4',10'-Tetrahydro-10'-hydroxy-10'-phenyl-spiro[cyclohexane-1,3'-pyrimido(1,2-a)indole]

(−)-Di-p-toluoyl-L-tartaric acid (40.44 g, 100.0mmol) was added rapidly, portionwise to a stirred suspension of the compound of Example 2 (33.25 g) in acetone (1L). The clear solution was stirred at room temperature for 15 h and the crystalline precipitate was filtered off, washed with acetone (2×50 ml) and dried to give (−)-2',3',4',10'-tetrahydro-10'-hydroxy-10'-phenylspiro[cyclo-hexane-1,3'-pyrimido(1,2-a)indole]as the (−)-di-ptoluoyltartrate (31.64g)m.p. 149° dec $[\alpha]_d-93°$ (ca 0.2% in EtOH). The combined filtrate and washings were concentrated in vacuo to give a pale brown crystalline residue, which was converted to the free base.

(+)-di-p-toluoyl-D-tartaric acid (23.05 g, 570 mmol) was added portionwise and rapidly to a stirred suspension of the free base enriched in the (+) enantiomer, in acetone (570 ml). The solution was stirred at room temperature for 15 h and the crystalline precipitate was filtered off, washed with acetone (2×50 ml) and dried to give (+)-2', 3', 4', 10'-tetrahydro-10'-hydroxy-10'-phenylspiro[cyclohexane-1,3'-pyrimido(1,2-a)indole]as the (+)-di-p-toluoyl tartrate (33.60 g) m.p. 149° C. dec., $[\alpha]_D+95°$ (ca 0.2% in EtOH).

Preparation of the hydrochlorides

The hydrochloride of each enantiomer was prepared by conversion of each di-p-toluoyltartrate to the free base. The resolved free bases were each suspended in absolute ethanol (200 ml), and the suspension was acidified with ethereal hydrogen chloride. The solution of each hydrochloride was concentrated in vacuo and the crystalline product was filtered off, washed with ethanol (2×20 ml) and dried under high vacuum at 50° C. for 15 h to give, in two crops,the hydrochloride of the (−)-enantiomer (11.57 g), m.p. 271° C. dec.,$[\alpha]_D-225°$ (ca 0.2% in CHCl₃) (Found: C,71.30; H,6.85; N,7.40; $C_{22}H_{24}N_2O.HCl$ requires: C,71.65; H,6.85; N, 7.60%), and the hydrochloride of the (+)-enantiomer (13.51 g), m.p. 269° C. dec., $[\alpha]_D+220°$ (ca 0.2% in CHCl₃).

Found: C,71.70; H,6.75; N,7.45; $C_{22}H_{24}N_2O.HCl$ requires: C,71.65; H,6.85; N,7.60%).

A second quantity (about 10%) of each enantiomer was obtained by reworking the mother liquors from the initial resolutions.

We claim:

1. A compound of the formula:

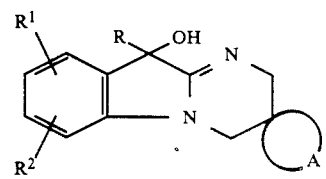

in which

R is alkyl of 1 to 6 carbon atoms, or substituted or unsubstituted phenyl naphtyhl, furyl, thienyl, pyridyl, indolyl or benzothienyl, in which the substituents are hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

$R^1$ and $R^2$ are, independently, hydrogen, hydroxyl, alkyl of 1 to 6 carbon alkoxy of 1 to 6 carbon atoms, haloalkyl of 1 to 6 carbon atoms, halo, amino, alkylamino of 1 to 6 carbon atoms or dialkylamino of 2 to 12 carbon atoms;

and

A, together with the carbon atom to which it is attached, completes a cyclopentane, cyclohexane or cycloheptane ring;

or a pharmaceutically acceptable salt thereof.

2. A compound of claim 1 in which R is alkyl of 1 to 6 carbon atoms, phenyl or substituted phenyl in which the substituent is halo, alkyl of 1 to 4 carbon atoms alkoxy of 1 to 4 carbon atoms or haloalkyl of 1 to 4 carbon atoms.

3. A compound of claim 2 in which A, taken with the carbon atom to which it is attached completes a cyclohexane ring.

4. A compound according to claim 1 which is 2',3',4',10'-tetrahydro-10,-hydroxy-10'-phenylspiro [cyclohexane-1,3'-pyrimido(1,2-a)indole] or a pharmaceutically acceptable acid addition salt thereof.

5. A compound of claim 1 which is 2',3',4',10'-tetrahydro-10'-hydroxy-10'-phenylspiro[cycloheptane-1,3'-pyrimido(1,2-a)indole] or a pharmaceutically acceptable salt thereof.

6. A compound of claim 1 which is 2',3',4',10,-tetrahydro-10'-butyl-10'-hydroxyspiro[cyclohexane-1,3'-pyrimido(1,2-a)indole] or a pharmaceutically acceptable salt thereof.

7. A compound of claim I which is 2',3',4',10 -tetrahydro-10'hydroxy-10'-phenylspiro[cyclopentane-1,3'- pyrimido(1,2-a)indole] or a pharmaceutically acceptable salt thereof.

8. A compound of claim 1 which is (−)-2′,3′,4′,10′-tetrahydro-10′-hydroxy-10′-phenylspiro[cyclohexane-1,3′-pyrimido(1,2-a)indole] or a pharmaceutically acceptable salt thereof.

9. A compound of claim 1 which is (+)-2′,3′,4′,10′-tetrahydro-10′-hydroxy-10′-phenylspiro[cyclohexane-1,3′-pyrimido(1,2-a)indole] or a phramaceutically acceptable salt thereof.

10. A method for treating diabetics which comprises administering to a mammal in need thereof, a hypoglycemically effective amount of a compound of formula:

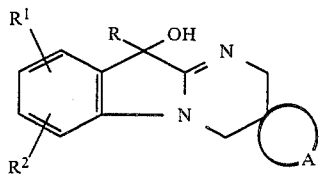

in which
R is alkyl of 1 to 6 carbon atoms, or substituted or unsubstituted phenyl, naphthyl, furyl, thienyl, pyridyl, indolyl or benzothienyl, in which the substituents are hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

$R^1$ and $R^2$ are, independently, hydrogen, hydroxyl, alkyl of 1 to 6 carbon alkoxy of 1 to 6 carbon atoms, haloalkyl of 1 to 6 carbon atoms, halo, amino, alkylamino of 1 to 6 carbon atoms or dialkylamino of 2 to 12 carbon atoms;
and
A, together with the carbon atom to which it is attached, completes a cyclopentane, cyclohexane or cycloheptane ring;
or a pharmaceutically acceptable salt thereof.

* * * * *

UNITED STATES PATENT OFFICE
CERTIFICATE OF CORRECTION

Patent No. 4,803,207                          Dated   February 7, 1989

Inventor(s) Alan C. White, Ian A. Cliffe, Richard S. Todd

It is certified that error appears in the above-identified patent and that said Letters Patent is hereby corrected as shown below:

In the Title, line 2, delete " 2',3',10' " and insert -- 2',3',4',10' --. In the Title, line 3, delete "CYCLOAKANE" and insert -- CYCLOALKANE --. In the Title, line 4, delete "DERATIVES" and insert -- DERIVATIVES --. In the ABSTRACT, line 5, delete "mormula" and insert -- formula --. In the ABSTRACT, lines 14-15, delete "hypoglyceamics" and insert -- hypoglycaemics --. Column 1, line 65, after "3-hydroxy" insert a hyphen --   -   --. Column 8, line 5, delete "$C_{18}H_2ON_2O_3$" and insert -- $C_{18}H_{20}N_2O_3$ --. Column 12, line 29, after "unsubstituted phenyl" insert a comma --,--. Column 12, line 29, delete "naphtyhl" and insert -- naphthyl --. Column 12, line 56, delete "10,-hydroxy" and insert -- 10'-hydroxy --. Column 13, lines 1-15, delete in their entirety and insert -- pyrimido (1,2-a)indole] or a pharmaceutically acceptable salt thereof.

8. A compound of Claim 1 which is (-)-2',3',4',10'-tetrahydro-10'-hydroxy-10'-phenylspiro[cyclohexane-1,3'-pyrimido(1,2-a)indole] or a pharmaceutically acceptable salt thereof.

9. A compound of Claim 1 which is (+)-2',3',4',10'- --.

UNITED STATES PATENT OFFICE
CERTIFICATE OF CORRECTION

Patent No. 4,803,207  Dated February 7, 1989

Inventor(s) Alan C. White, Ian A. Cliffe, Richard S. Todd

It is certified that error appears in the above-identified patent and that said Letters Patent is hereby corrected as shown below:

Column 14, line 1, insert --

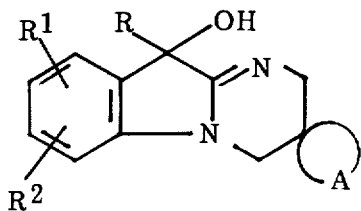

Column 14, line 19, after "alkyl of 1 to 6 carbon" insert -- atoms, --.

Signed and Sealed this

Thirteenth Day of February, 1990

*Attest:*

JEFFREY M. SAMUELS

*Attesting Officer*  *Acting Commissioner of Patents and Trademarks*